United States Patent [19]
Wright

[11] Patent Number: 5,989,264
[45] Date of Patent: Nov. 23, 1999

[54] ULTRASONIC POLYP SNARE

[75] Inventor: John C. Wright, Loveland, Ohio

[73] Assignee: Ethicon Endo-Surgery, Inc., Cincinnati, Ohio

[21] Appl. No.: 09/095,904

[22] Filed: Jun. 11, 1998

[51] Int. Cl.⁶ .......................... A61B 17/24; A61B 17/22
[52] U.S. Cl. .................. 606/113; 606/110; 604/22
[58] Field of Search ................... 606/110, 113, 606/114, 128, 131, 167, 170; 604/22

[56] References Cited

U.S. PATENT DOCUMENTS

| | | | |
|---|---|---|---|
| 4,646,742 | 3/1987 | Packard et al. | 128/344 |
| 4,867,141 | 9/1989 | Nakada et al. | 128/24 A |
| 5,035,696 | 7/1991 | Rydell | 606/47 |
| 5,057,107 | 10/1991 | Parins et al. | 606/48 |
| 5,078,717 | 1/1992 | Parins et al. | 606/48 |
| 5,125,928 | 6/1992 | Parins et al. | 606/48 |
| 5,158,561 | 10/1992 | Rydell et al. | 606/113 |
| 5,192,280 | 3/1993 | Parins | 606/48 |
| 5,192,286 | 3/1993 | Phan et al. | 606/127 |
| 5,197,964 | 3/1993 | Parins | 606/48 |
| 5,201,732 | 4/1993 | Parins et al. | 606/47 |
| 5,217,458 | 6/1993 | Parins | 606/48 |
| 5,248,296 | 9/1993 | Alliger | 609/22 |
| 5,254,115 | 10/1993 | Bhatta et al. | 606/16 |
| 5,263,957 | 11/1993 | Davison | 606/169 |
| 5,304,115 | 4/1994 | Flueger et al. | 604/22 |
| 5,326,342 | 7/1994 | Pflueger et al. | 604/22 |
| 5,376,094 | 12/1994 | Kline | 606/113 |
| 5,379,301 | 1/1995 | Sato et al. | 371/19 |
| 5,397,293 | 3/1995 | Alliger et al. | 601/2 |
| 5,603,711 | 2/1997 | Parins et al. | 606/51 |
| 5,772,676 | 6/1998 | Cuschieri et al. | 606/167 |

FOREIGN PATENT DOCUMENTS

| | | |
|---|---|---|
| 9-276274 | 10/1997 | Japan . |
| 10057391 | 3/1998 | Japan . |
| WO 97/40759 A1 | of 0000 | WIPO . |

*Primary Examiner*—Paul J. Hirsch
*Assistant Examiner*—Michael B. Priddy
*Attorney, Agent, or Firm*—Bernard E. Shay

[57] ABSTRACT

In one embodiment the present invention comprises an ultrasonic polyp snare adapted to grasp, cut and coagulate polyps and other tissue masses in internal body lumens, specifically in the colon. An ultrasonic polyp snare according to the present invention includes an ultrasonic signal generator attached to the proximal end of a flexible ultrasonic waveguide. An ultrasonic vibration amplifier is coupled to the distal end of the flexible ultrasonic waveguide. An ultrasonic blade is coupled to the ultrasonic amplifier. An ultrasonic attenuator is coupled to the distal end of the ultrasonic blade. And, a snare wire is positioned adjacent at least a portion of the ultrasonic blade.

15 Claims, 5 Drawing Sheets

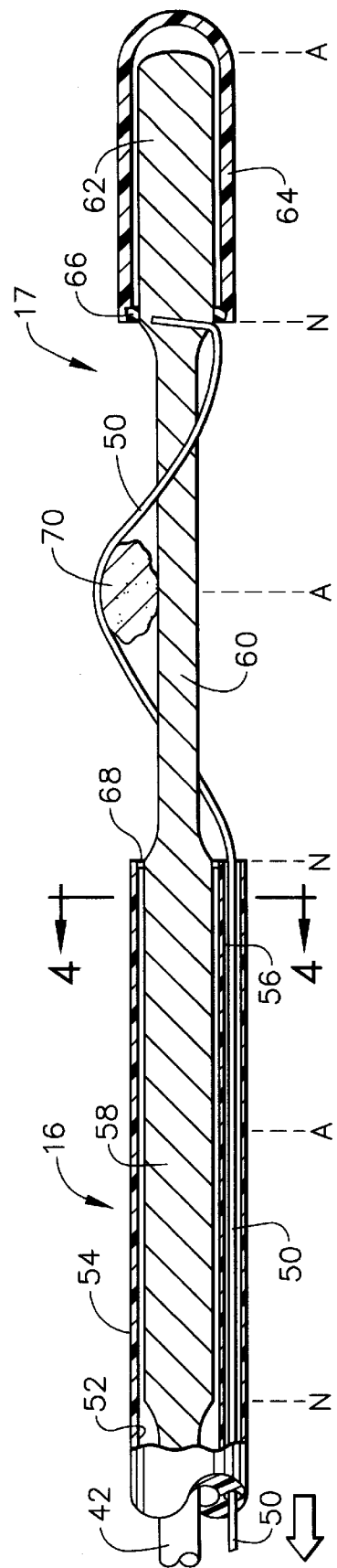
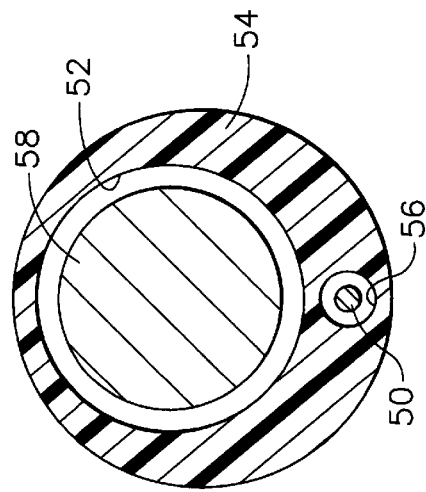
FIG. 3
FIG. 4

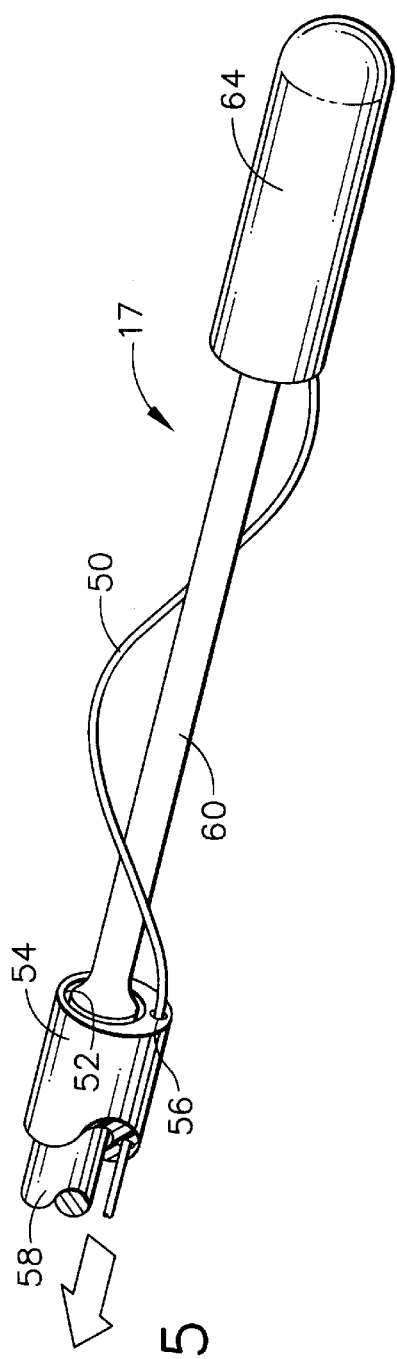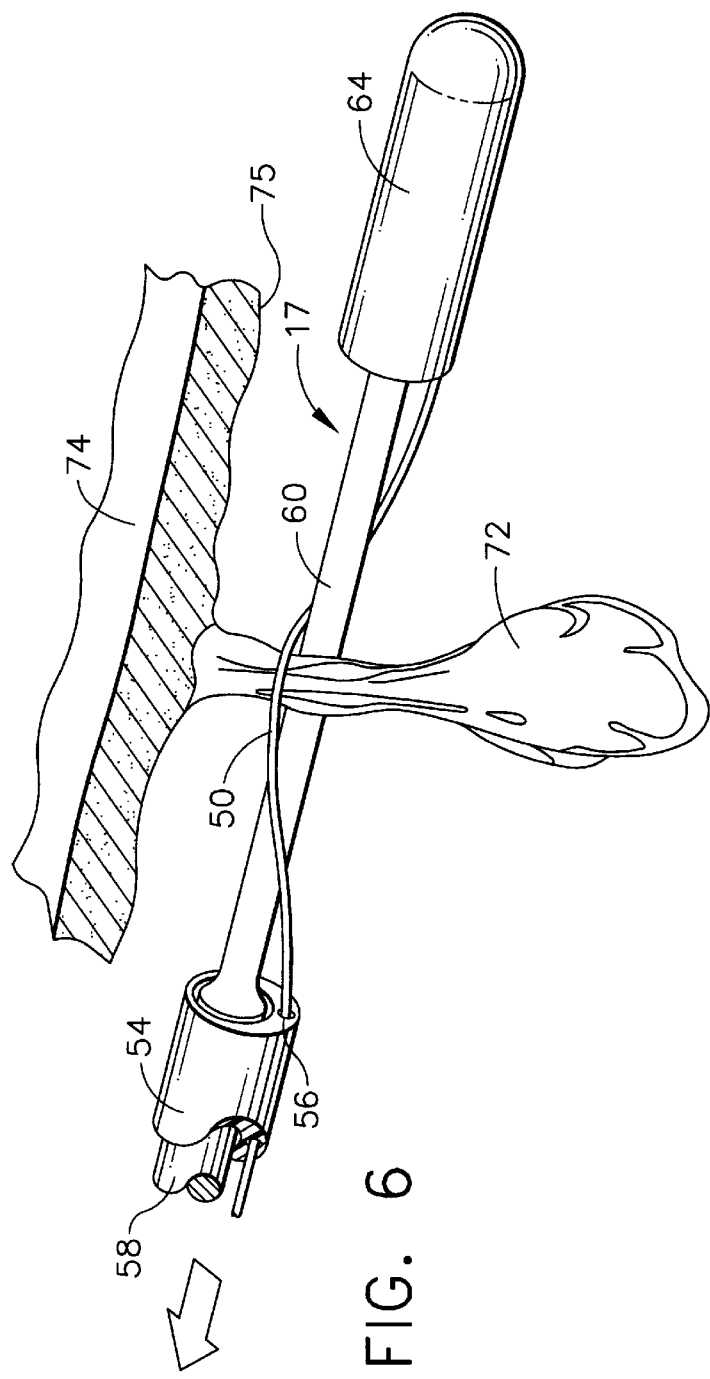
FIG. 5
FIG. 6

ULTRASONIC POLYP SNARE

This application is related to the following copending patent applications: application Ser. No. 09/059,472, filed Apr. 13, 1998, and application Ser. No. 09/059,072, filed Apr. 13, 1998, which are hereby incorporated herein by reference.

FIELD OF THE INVENTION

The present invention relates, in general, to an ultrasonic surgical instrument and, more particularly, to an ultrasonic polyp snare designed to grasp, cut and coagulate polyps in the intestine.

BACKGROUND OF THE INVENTION

The use of ultrasonically actuated surgical instruments has proven to be a safe and effective method of cutting and coagulating tissue in a number of surgical procedures. One procedure which could benefit from the use of ultrasonic surgical instruments is the removal of tissue from the interior lining of certain lumens in the human body. Specifically, the removal of polyps from the interior lining of the colon. Surgical procedures for the removal of polyps are generally referred to as "polypectomys". In performing a polypectomy in the colon, the surgeon normally inserts a scope, such as a colonoscope, which is adapted to allow the surgeon to visually inspect the interior of the colon and to excise tissue, including polyps, where appropriate. Instruments such as colonoscopes may include a lumen to allow the surgeon to guide certain flexible surgical instruments to the treatment site. Such surgical instruments may be used to, for example, selectively remove polyps from the internal lining of the colon.

When removing a polyp from the colon it is preferable to cut the polyp stem as close as possible to the internal lining of the colon without damaging the lining. It is further preferable to stop or minimize any bleeding which may result from the removal of the polyp, in order to minimize the potential for infection or other undesirable consequences. It would, therefore, be advantageous to design an ultrasonic surgical instrument particularly adapted for removing polyps from the internal lining of the colon. It would further be advantageous to design an ultrasonic instrument adapted for removing polyps from the internal lining of the colon without damaging the internal lining. It would also be advantageous to design an ultrasonic instrument adapted for removing polyps from the internal lining of the colon wherein the polyp stem tissue was coagulated as the polyp stem was being cut.

SUMMARY OF THE INVENTION

In one embodiment the present invention comprises an ultrasonic polyp snare adapted to grasp, cut and coagulate polyps and other tissue masses in internal body lumens, specifically in the colon. An ultrasonic polyp snare according to the present invention includes an ultrasonic signal generator attached to the proximal end of a flexible ultrasonic waveguide. An ultrasonic vibration amplifier is coupled to the distal end of the flexible ultrasonic waveguide. An ultrasonic blade is coupled to the ultrasonic amplifier. An ultrasonic attenuator is coupled to the distal end of the ultrasonic blade. And, a snare wire is positioned adjacent at least a portion of the ultrasonic blade.

In an ultrasonic polyp snare according to the present invention, the snare wire may be affixed to the polyp snare at the ultrasonic attenuator. The ultrasonic polyp snare extends proximally from the ultrasonic attenuator to the proximal end of the ultrasonic waveguide. The snare wire may further be operatively connected to an actuation trigger located at the proximal end of the ultrasonic waveguide. Alternatively, in the present invention, the snare wire may be replaced by a band having a rectangular cross section.

In an ultrasonic polyp snare according to the present invention, the ultrasonic vibration amplifier comprises a step increase in diameter at the distal end of the ultrasonic waveguide and a step decrease in diameter at the proximal end of the ultrasonic blade. The step increase is preferably positioned at a vibratory node of the ultrasonic waveguide and the step decrease is preferably positioned at least one half wavelength away from the step increase. More specifically, the step decrease is generally n half-wavelengths from the step increase, where n is any whole number.

In an ultrasonic polyp snare according to the present invention, the ultrasonic blade is preferably rigid. Further, the ultrasonic blade is preferably one-half wavelength long with an antinode at its center. More specifically, the ultrasonic blade is generally x half-wavelengths long where x is any whole number.

In an ultrasonic polyp snare according to the present invention, the proximal end of the ultrasonic attenuator comprises a step increase in diameter at the distal end of the ultrasonic blade. The proximal end of the ultrasonic attenuator is preferably positioned at a vibratory node of the ultrasonic blade. The ultrasonic attenuator preferably terminates one-quarter wavelength from the end of the ultrasonic blade. More specifically, the ultrasonic attenuator is generally m quarter-wavelengths long, where m is any odd whole number. Further, the ultrasonic attenuator of the present invention may be substantially covered by an outer protective sheath. An ultrasonic attenuator according to the present invention may comprise a one-quarter wavelength mass positioned at the distal end of the ultrasonic blade.

In an ultrasonic polyp snare according to the present invention, the ultrasonic waveguide may be positioned in a flexible catheter which extends from the proximal end of the ultrasonic waveguide to the proximal end of the ultrasonic blade. A flexible catheter according to the present invention may further include first and second lumens wherein said ultrasonic waveguide is positioned in the first lumen and the snare wire is positioned in the second lumen.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 3 is an enlarged sectional view of the distal end of the ultrasonic polyp snare illustrated in FIG. 2.

FIG. 4 is a section view taken along line 4—4 of FIG. 3.

FIG. 5 is an isometric view of the end effector of the ultrasonic polyp snare illustrated in FIG. 1.

FIG. 6 is an isometric view of the end effector of the ultrasonic polyp snare illustrated in FIG. 1, wherein a polyp is grasped by the snare wire of the instrument.

DETAILED DESCRIPTION OF THE INVENTION

Figure 1:
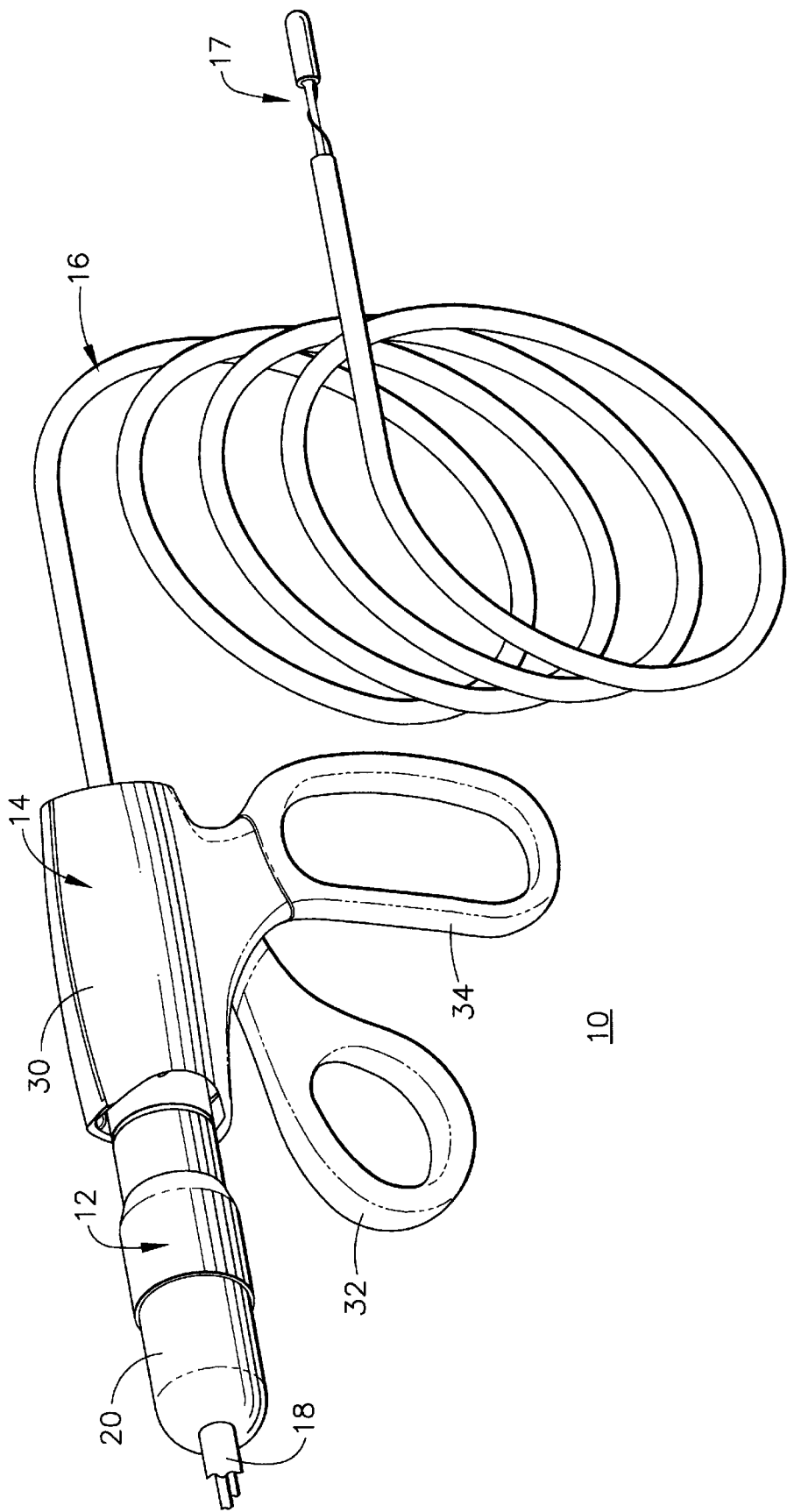
FIG. 1 is an illustration of an ultrasonic polyp snare according to the present invention.

FIG. 1 is an illustration of an ultrasonic polyp snare used to grasp and remove polyps from the intestinal wall of a surgical patient. The polyp snare illustrated in FIG. 1 utilizes ultrasonic energy to cut the polyp stem and coagulate tissue on either side of the cut line. In the embodiment of the invention illustrated in FIG. 1, ultrasonic polyp snare 10 includes ultrasonic signal generator 12, instrument handle 14, ultrasonic catheter 16 and ultrasonic end effector 17. Ultrasonic signal generator 12 includes generator housing 20 and signal cable 18. A suitable ultrasonic signal generator is available from Ethicon Endo-Surgery, Inc. under the trade name HARMONIC SCALPEL™, Model. Ultrasonic signal generator 12 is mounted in instrument handle 14. Instrument handle 14 includes instrument housing 30, actuation trigger 32 and finger grip 34. Ultrasonic catheter 16 extends from the distal end of instrument handle 14 to ultrasonic end effector 17. Ultrasonic end effector 17 is positioned at the distal end of ultrasonic catheter 16.

Figure 2:
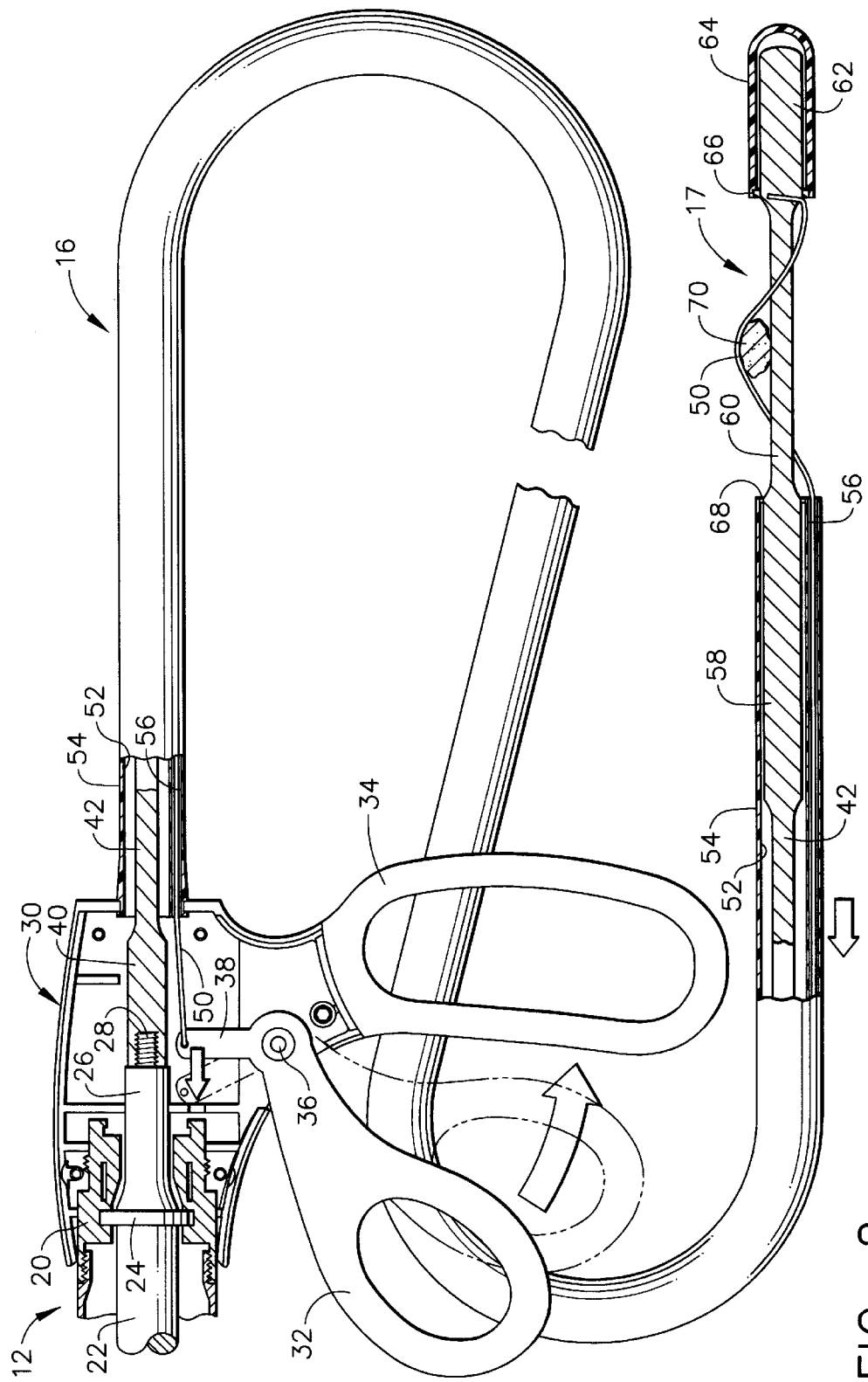
FIG. 2 is a partial section side elevation view of the ultrasonic polyp snare illustrated in FIG. 1.

FIG. 2 is a partial sectional side elevation view of the ultrasonic polyp snare illustrated in FIG. 1. In FIG. 2 only a portion of the distal end of ultrasonic signal generator 12 is visible. The visible portion of ultrasonic signal generator 12 in FIG. 2 includes generator housing 20, transducer output waveguide 22, generator output amplifier 26 and threaded coupling stud 28. The proximal end of ultrasonic catheter 16 is threaded on to threaded coupling stud 28 at the distal end of generator output amplifier 26. Isolation mount 24 is positioned to acoustically isolate transducer output waveguide 22 and generator output amplifier 26 from generator housing 20. Instrument housing 30 includes actuation trigger 32, finger grip 34, pivot pin 36 and actuation pivot arm 38. Ultrasonic catheter 16 includes proximal waveguide amplifier 40, ultrasonic waveguide 42, snare wire 50, waveguide lumen 52, catheter sheath 54, actuator lumen 56 and ultrasonic vibration amplifier 58. Ultrasonic end effector 17 includes ultrasonic blade 60, ultrasonic attenuator 62, attenuator sheath 64 and snare wire 50. Isolation mounts 66 and 68 are positioned at the distal and proximal ends of ultrasonic blade 60, respectively. In the embodiment of the invention illustrated in FIG. 2, snare wire 50 is wrapped once around ultrasonic blade 60 to facilitate the positioning of tissue mass 70 against ultrasonic blade 60. Ultrasonic attenuator 62 is positioned at the distal end of ultrasonic blade 60 and is surrounded by attenuator sheath 64. Ultrasonic attenuator 62 is preferably a mass approximately one-quarter wavelength long, beginning at a node and ending at an antinode. Ultrasonic attenuator 62 may be any number of odd wavelengths long.

FIG. 3 is an enlarged sectional view of the distal end of the ultrasonic polyp snare illustrated in FIG. 2. In the embodiment of the invention illustrated in FIG. 3, flexible ultrasonic waveguide 42 is preferably connected to ultrasonic vibration amplifier 58 at a transverse vibrational null point or node of the waveguide. Ultrasonic vibration amplifier 58, preferably being one-half wavelength long, preferably terminates at a second node point where ultrasonic vibration amplifier 58 is connected to ultrasonic blade 60. The proximal end of ultrasonic vibration amplifier 58 is delineated by a step increase in waveguide diameter while the distal end of ultrasonic vibration amplifier 58 is delineated by a step decrease in waveguide diameter. As used herein, a step increase may define any number of abrupt or tapered transitions in waveguide diameter but preferably defines a tapered transition. It will be apparent that ultrasonic vibration amplifier 58 may be any number of half wavelengths long, and preferably starts and ends at node points. Ultrasonic vibration amplifier 58 is positioned in waveguide lumen 52, and is held in place by isolation mount 68 which may comprise, for example, a silicone O-ring or other suitable isolation mount.

Snare wire 50 extends through actuator lumen 56 to the distal end of ultrasonic catheter 16 and out the distal end of actuator lumen 56 where snare wire 50 wraps once around ultrasonic blade 60. In the illustrated embodiment, the distal end snare wire 50 is affixed to ultrasonic attenuator 62 at the distal end of ultrasonic blade 60. Snare wire 50 may be any suitable material including a polymer or kevlar wire having a round or flat cross-section.

Ultrasonic blade 60 extends from the distal end of ultrasonic vibration amplifier 58 to the proximal end of ultrasonic attenuator 62. In the embodiment of the invention illustrated in FIG. 3, ultrasonic blade 60 is also one-half wave length long. Ultrasonic blade 60 preferably begins at the terminal node of ultrasonic vibration amplifier 58 and terminates at a second node, with at least one anti-node in its central portion. In the embodiment of FIG. 3, tissue 70 is pulled against ultrasonic blade 60 by snare wire 50 at the interior antinode of ultrasonic blade 60. Ultrasonic attenuator 62 is surrounded by attenuator sheath 64, which is positioned away from the surface of ultrasonic attenuator 62 by isolation mount 66. Isolation mount 66 may comprise, for example, a silicone O-ring or other suitable isolation mount.

FIG. 4 is a sectional view taken along line 4—4 of FIG. 3. As illustrated in FIG. 4, waveguide lumen 52 contains ultrasonic vibration amplifier 58 and actuator lumen 56 contains snare wire 50. Waveguide lumen 52 and actuator lumen 56 are positioned in catheter sheath 54. Waveguide lumen 52 and actuator lumen 56 extend from the proximal end of catheter sheath 54 to the distal end of catheter sheath 54. Catheter sheath 54 may be manufactured from any suitable material including poytetrafluoroethylene, silicon or polyethylene.

Figure 7:
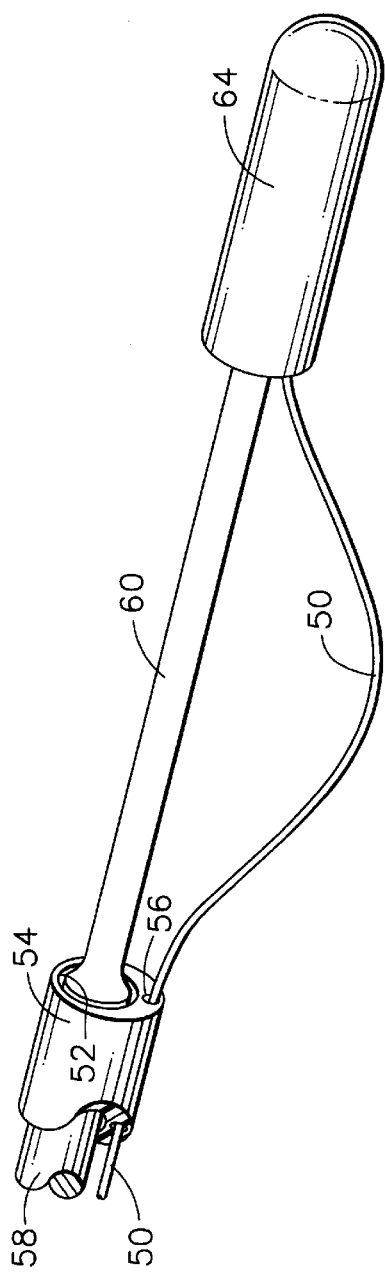
FIG. 7 is an alternate embodiment of the end effector of the ultrasonic polyp snare illustrated in FIG. 1, wherein the snare wire is parallel to the axis of the ultrasonic blade.

FIG. 5 is an isometric view of the end effector of the ultrasonic polyp snare illustrated in FIG. 1, further illustrating ultrasonic end effector 17. FIG. 6 is an isometric view of an end effector of the instrument illustrated in FIG. 1 wherein a polyp 72 is grasped by snare wire 50. In FIG. 6, polyp 72 is positioned against ultrasonic blade 60 by snare wire 50 which, when pulled in a proximal direction by distal movement of actuation trigger 32 is forced against the outer surface of ultrasonic blade 60. Attenuator sheath 64 prevents ultrasonic attenuator 62 from contacting the interior lining 75 of intestine 74, thus preventing ultrasonic end effector 17 from damaging intestine 74 when polyp 72 is cut and removed. FIG. 7 is an alternate embodiment of the end effector of the surgical instrument illustrated in FIG. 1 wherein snare wire 50 is parallel to the axis of the waveguide.

Figure 8:
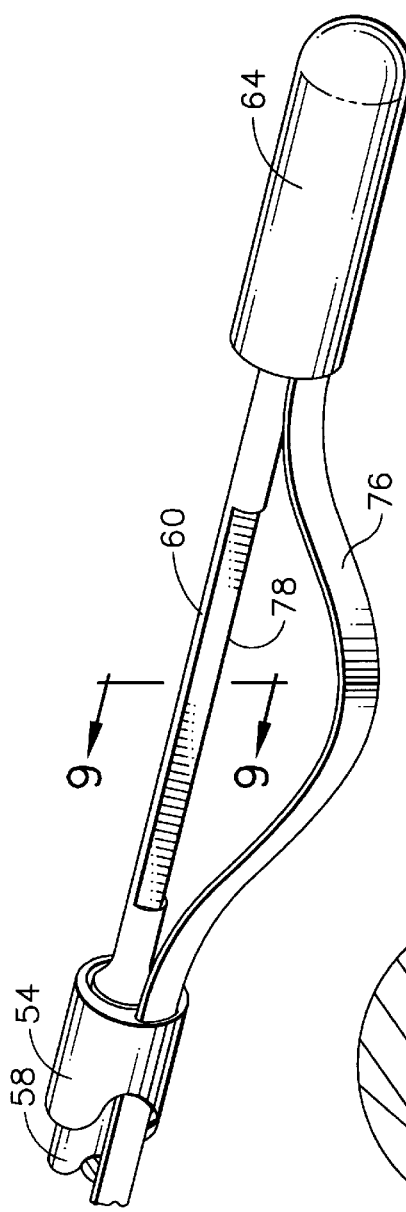
FIG. 8 is a further alternate embodiment of the end effector of the ultrasonic polyp snare illustrated in FIG. 1, including a snare band having a rectangular cross-section.
Figure 9:
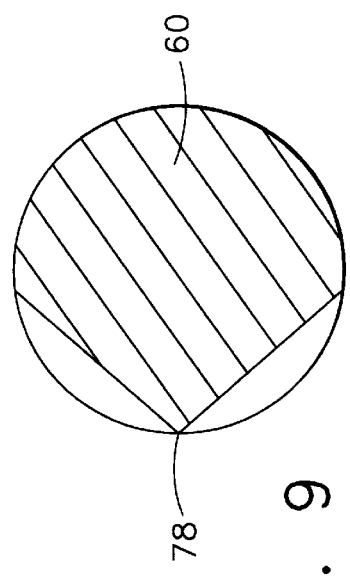
FIG. 9 is a cross-sectional view of the ultrasonic blade of the polyp snare end effector illustrated in FIG. 8, wherein the section is taken along line 9—9.

FIG. 8 is a further alternative embodiment of the end effector of the surgical instrument illustrated in FIG. 1 wherein snare band 76 is a member having a rectangular cross section. FIG. 9 is a sectional view of the ultrasonic blade illustrated in FIG. 8 taken along line 9—9. In the embodiment illustrated in FIG. 8, ultrasonic blade edge 78 is positioned to facilitate the cutting of tissue positioned against the surface of ultrasonic blade edge 78. As is also illustrated in FIG. 8, a snare band 76 may be used to replace snare wire 50 to provide additional strength. In the embodiment of FIG. 8, snare band 76 is positioned opposite blade edge 78 of blade 60.

In operation, ultrasonic catheter 16 is placed into the intestine of a human patient by, for example, inserting catheter 16 through a suitable scope such as a colonoscope. It is, therefore, preferable that ultrasonic catheter 16, including ultrasonic flexible waveguide 42 be flexible enough to pass through the intestine. Ultrasonic end effector 17 is placed next to a tissue mass 70, such as polyp 72, which the surgeon wishes to remove. Tissue mass 70 is then positioned between blade 60 and snare wire 50. Distal movement of actuation trigger 32 towards finger grip 34 results in proximal movement of snare wire 50 which is connected to actuation pivot arm 38. Proximal movement of snare wire 50 pulls snare wire 50 and tissue mass 70 against ultrasonic blade 60. It is, therefore, preferable that ultrasonic blade 60 be rigid in order to prevent ultrasonic blade 60 from bending away from tissue 70 as snare wire 50 is tightened. Ultrasonic blade 60 is actuated by supplying electrical power to ultrasonic signal generator 12 through signal cable 18 at an appropriate frequency, such as, for example, 55 kilohertz. The electrical signal supplied through signal cable 18 is applied to transducers (e.g. piezoelectric transducers) in ultrasonic signal generator 12. The transducers (not shown) convert the electrical signals supplied through signal cable 18 to mechanical vibrators. The ultrasonic mechanical vibrations generated by ultrasonic signal generator 12 are passed through transducer output waveguide 22 to generator output amplifier 26. Generator output amplifier 26 is connected by threaded coupling stud 28 to proximal waveguide amplifier 40. Ultrasonic mechanical energy is then transmitted from proximal waveguide amplifier 40 to flexible ultrasonic waveguide 42 which, in turn, transmits the ultrasonic energy to ultrasonic vibration amplifier 58. The proximal end of ultrasonic vibration amplifier 58 amplifies the input ultrasonic signal to ultrasonic blade 60. Thus, exciting ultrasonic blade 60 and cutting tissue 70 positioned against the blade by snare wire 50 or snare band 76. Further, since the mechanical ultrasonic energy is beneficial in facilitating the coagulation of blood vessels in tissue mass 70, the tissue mass 70 may be removed with a minimal amount of bleeding. Ultrasonic attenuator 62, which is positioned at the distal end of ultrasonic blade 60 acts to attenuate the mechanical ultrasonic vibrations by including a step up in waveguide diameter at the node which is located at the distal end of ultrasonic blade 60 and a termination point at the next anti-node.

It will be apparent to those skilled in the art that the wavelength of the mechanical vibrations and, thus, the position of nodes and antinodes will be a function of the material selected, for example, flexible ultrasonic waveguide 42, ultrasonic vibration amplifier 58, ultrasonic blade 60 and ultrasonic attenuator 62. Preferable materials may include, for example, solid titanium alloy (e.g. Ti-6Al-4V) or aluminum. In solid titanium alloy rod at 55.5 kHz the longitudinal vibratory wavelength would be approximately 3.2 inches, making each node in the system approximately 1.6 inches apart.

It will further be apparent that the use of ultrasound in a polyp snare is beneficial for a number of reasons. In particular, using an ultrasonic polyp snare, the tissue in the polyp stem is coagulated as the stem is cut. Further, using an ultrasonic blade eliminates the potential for stray electrical currents which may result from using monopolar or bipolar electrosurgical instruments. Using an ultrasonic blade will also reduce or eliminate the eschar which can build up on electrosurgical instruments and reduce or eliminate tissue sticking. Visibility is also improved because the ultrasonic blade does not generate vapor or smoke as some electrosurgical instruments may, thus improving visibility.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An ultrasonic polyp snare comprising:
   an ultrasonic signal generator;
   a flexible ultrasonic waveguide having a proximal end and a distal end, wherein said proximal end is operatively coupled to said ultrasonic generator;
   an ultrasonic vibration amplifier coupled to said distal end of said ultrasonic waveguide;
   a rigid ultrasonic blade having a proximal end and a distal end, wherein said proximal end is coupled to said ultrasonic amplifier;
   an ultrasonic attenuator coupled to the distal end of said rigid ultrasonic blade;
   a snare wire positioned adjacent at least a portion of said rigid ultrasonic blade.

2. An ultrasonic polyp snare as set forth in claim 1 wherein said snare wire is affixed to said polyp snare at said ultrasonic attenuator and extends proximally from said ultrasonic attenuator to said proximal end of said ultrasonic waveguide.

3. An ultrasonic polyp snare as set forth in claim 2 wherein said snare wire wraps at least once around said ultrasonic blade.

4. An ultrasonic polyp snare as set forth in claim 2 wherein said ultrasonic vibration amplifier comprises a step increase in diameter at the distal end of said flexible ultrasonic waveguide and a step decrease in diameter at said proximal end of said ultrasonic blade is connected to said step decrease in amplitude.

5. An ultrasonic polyp snare according to claim 2 wherein said ultrasonic attenuator comprises a step increase in diameter at said distal end of said ultrasonic blade and said ultrasonic blade ends approximately one-quarter wavelength from said distal end of said ultrasonic blade.

6. An ultrasonic polyp snare comprising:
   an ultrasonic signal generator;
   an handle including an actuation trigger;
   a flexible catheter extending from said ultrasonic generator wherein said flexible catheter has a proximal end and a distal end;
   an ultrasonic end effector operatively connected to said flexible catheter, wherein said ultrasonic end effector comprises:
   an ultrasonic blade having a proximal end and a distal end, wherein said proximal end is operatively connected to said distal end of said flexible catheter; and
   a snare wire adjacent said ultrasonic blade, wherein said snare wire passes through said flexible catheter and is operatively connected to said actuation trigger; and an ultrasonic attenuator operatively connected to said distal end of said ultrasonic blade.

7. An ultrasonic polyp snare according to claim 6 wherein said flexible catheter comprises:

an outer shell including a first lumen; and a flexible ultrasonic waveguide having a proximal end and a distal end, wherein said ultrasonic waveguide extends through said first lumen from said handle to said ultrasonic blade.

8. An ultrasonic polyp snare according to claim 7 wherein said flexible ultrasonic waveguide further comprises an ultrasonic vibration amplifier positioned at said distal end of said flexible ultrasonic waveguide directly proximal to said ultrasonic blade.

9. An ultrasonic polyp snare according to claim 8 wherein said ultrasonic attenuator comprises a one-quarter wavelength mass positioned at the distal end of said ultrasonic blade and wherein at least a portion of said mass has a diameter greater than an outer diameter of said ultrasonic blade.

10. An ultrasonic polyp snare according to claim 8 wherein said ultrasonic amplifier is approximately one-half wavelength long.

11. An ultrasonic polyp snare end effector operatively attached to a flexible ultrasonic transmission waveguide having a proximal end and a distal end, wherein said end effector comprises:

an ultrasonic vibration amplifier positioned at said distal end of said ultrasonic transmission waveguide, wherein said ultrasonic vibration amplifier has a proximal end operatively connected to said ultrasonic transmission waveguide and a distal end;

a rigid ultrasonically actuated blade positioned at said distal end of said ultrasonic transmission waveguide, wherein said ultrasonically actuated blade has a proximal end operatively connected to said ultrasonic vibration amplifier and a distal end;

an ultrasonic attenuator having a proximal end and a distal end, wherein said proximal end is operatively connected to said distal end of said rigid ultrasonically actuated blade; and a snare wire operatively connected to said ultrasonic blade.

12. An end effector according to claim 11 wherein said ultrasonic amplifier comprises:

a first transition at a first node, said ultrasonic amplifier having a greater diameter than said flexible transmission waveguide distal to said first node;

a second transition at a second node, said ultrasonically actuated blade being affixed to said second node and said ultrasonic amplifier having a diameter larger than said ultrasonic blade proximal to said second node.

13. An end effector according to claim 12 wherein said ultrasonic attenuator comprises:

a third transition at a third node, wherein said third node is positioned at said distal end of said ultrasonic blade, said ultrasonic attenuator being greater in diameter than said ultrasonically actuated blade distal to said third transition;

a fourth transition at an antinode of said ultrasonic attenuator, wherein said fourth transition is at said distal end of said ultrasonic attenuator.

14. An end effector according to claim 12 wherein said first transition and said second transition are n/2 wavelengths apart, n being any whole number.

15. An end effector according to claim 13 wherein said third transition and said fourth transition are m/4 wavelengths apart, m being any odd whole number.

* * * * *